United States Patent
Lee et al.

(10) Patent No.: US 10,803,158 B2
(45) Date of Patent: *Oct. 13, 2020

(54) VARIABLE BIOMETRIC INFORMATION-BASED AUTHENTICATION SYSTEM AND AUTHENTICATION METHOD USING THE SAME

(71) Applicants: Jin Hyuk Lee, Seoul (KR); FORC&C CO., LTD., Seoul (KR)

(72) Inventors: Jin Hyuk Lee, Seoul (KR); Yoon Hee Koo, Seoul (KR)

(73) Assignees: Jin Hyuk Lee, Seoul (KR); FORC&C CO., LTD., Seoul (KR)

( * ) Notice: Subject to any disclaimer, the term of this patent is extended or adjusted under 35 U.S.C. 154(b) by 305 days.

This patent is subject to a terminal disclaimer.

(21) Appl. No.: 15/763,721

(22) PCT Filed: Oct. 30, 2017

(86) PCT No.: PCT/KR2017/012046
§ 371 (c)(1),
(2) Date: Mar. 27, 2018

(87) PCT Pub. No.: WO2018/169159
PCT Pub. Date: Sep. 20, 2018

(65) Prior Publication Data
US 2019/0392125 A1 Dec. 26, 2019

(30) Foreign Application Priority Data
Mar. 17, 2017 (KR) .................. 10-2017-0033830

(51) Int. Cl.
*G06F 21/32* (2013.01)
*H04W 12/06* (2009.01)
(Continued)

(52) U.S. Cl.
CPC ............ *G06F 21/32* (2013.01); *A61B 5/04* (2013.01); *G06F 21/45* (2013.01); *H04W 12/002* (2019.01); *H04W 12/0608* (2019.01)

(58) Field of Classification Search
CPC ...... G06F 21/32; G06F 21/45; H04W 12/002; H04W 12/0608
(Continued)

(56) References Cited

U.S. PATENT DOCUMENTS

| 2009/0144804 A1 | 6/2009 | Idicula et al. |
| 2013/0227651 A1* | 8/2013 | Schultz .................. G06F 21/32 726/4 |
| 2014/0188770 A1 | 7/2014 | Agrafioti et al. |

FOREIGN PATENT DOCUMENTS

| JP | 2007-213196 A | 8/2007 |
| JP | 2007-265219 A | 10/2007 |

(Continued)

OTHER PUBLICATIONS

International Search Report in International Application No. PCT/KR2017/012046, filed Oct. 30, 2017.
(Continued)

*Primary Examiner* — Brandon S Hoffman
*Assistant Examiner* — Nega Woldemariam
(74) *Attorney, Agent, or Firm* — Saliwanchik, Lloyd & Eisenschenk

(57) ABSTRACT

An authentication system that uses personal variable biometric information which changes according to times and environments, and an authentication method using the same are disclosed. The variable biometric information-based authentication system includes: a mobile terminal configured to generate information regarding an ID that intends to access a facility or information requiring an access authority,
(Continued)

and to collect variable biometric information, such that information regarding the ID and the variable biometric information are stored all together; and a variable biometric information management server configured to, when the mobile terminal requests a login command regarding the ID, verify validity of the login command regarding the ID based on the variable biometric information. Accordingly, a real data value of collected biometric information is not used in the authentication procedure, and the authentication procedure is performed only by using a figure or a form of a graph indicating a variation in a specific section or a data arithmetic value obtained by performing a predetermined arithmetic operation with respect to the real data value. Therefore, even if the biometric information used in the authentication procedure is leaked, a damage resulting therefrom can be inhibited. In addition, since a security level of the authentication procedure can be selectively determined, the security of the authentication procedure can be enhanced by combining different types of variable biometric information or by combining variable biometric information of a plurality of users. In addition, as the security level of the authentication procedure is selectively determined, the authentication procedure can be diversely utilized in an entering authentication to a facility such as an office or school or secure authentication in financial services such as account transfer, payment, etc.

9 Claims, 9 Drawing Sheets

(51) Int. Cl.
  *H04W 12/00* (2009.01)
  *A61B 5/04* (2006.01)
  *G06F 21/45* (2013.01)

(58) Field of Classification Search
  USPC .......................................................... 713/186
  See application file for complete search history.

(56) References Cited

FOREIGN PATENT DOCUMENTS

| | | |
|---|---|---|
| JP | 2008-064928 A | 3/2008 |
| JP | 2012-212362 A | 11/2012 |
| KR | 10-2002-0081121 A | 10/2002 |
| KR | 10-1756059 B1 | 7/2017 |
| WO | WO-2015/039084 A1 | 3/2015 |

OTHER PUBLICATIONS

Supplementary European Search Report dated May 6, 2020 in European Application No. 17859365.3.

* cited by examiner

VARIABLE BIOMETRIC INFORMATION-BASED AUTHENTICATION SYSTEM AND AUTHENTICATION METHOD USING THE SAME

CROSS-REFERENCE TO RELATED APPLICATIONS

This application is the U.S. national stage application of International Patent Application No. PCT/KR2017/012046, filed Oct. 30, 2017, which claims priority to Korean Application No. 10-2017-0033830, filed Mar. 17, 2017, the disclosures of each of which are incorporated herein by reference in their entirety.

TECHNICAL FIELD

The present disclosure relates to a variable biometric information-based authentication system and an authentication method using the same, and more particularly, to an authentication system that uses personal variable biometric information which changes according to times and environments, and an authentication method using the same.

BACKGROUND ART

In general, a user of a computer needs to perform an authentication procedure to have an access authority by inputting his/her ID and password into a host computer or a network, in order to access limited information or to use a membership service.

Such an authentication procedure may be performed between a system manager and a user, as a means for identifying, managing, and securing an authorized person, in a specific computer system or a plurality of user computer systems which require secret protection. In recent years, the authentication procedure is increasingly used in various fields, from the field of generating records of going in and out a facility such as an office, records of starting and ending work, or records of attendance at class, to the online financial service field with the development of electronic commerce, and there is an increasing demand for a simpler and safer authentication procedure.

Specifically, through a door lock authentication procedure through fingerprint recognition, the records of going in and out an office may be generated and this may be reflected on the records of starting and ending work, and also, mobile unlocking or password setting, and various personal authentication, and personal identification systems and methods based on iris recognition, which has a higher identification accuracy than that of fingerprint recognition, as well as based on biometric information authentication through fingerprint recognition, are appearing.

However, such biometric information authentication systems and methods have limits since biometric information used therein is unique to each individual person, but is permanent and thus has the risk of being leaked and illegally used.

Therefore, there is a need for new concept authentication system and method which can minimize a damage even if biometric information is leaked.

DISCLOSURE

Technical Problem

The present disclosure has been developed in order to address the above-discussed deficiencies of the prior art, and an object of the present disclosure is to provide a variable biometric information-based authentication system, which can selectively determine a security level of an authentication procedure, and performs the authentication procedure using personal variable biometric information, which changes according to times and environments, so as to inhibit a damage if the biometric information used in the authentication procedure is leaked, and an authentication method using the same.

In addition, another object of the present disclosure is to provide a variable biometric information-based authentication system, which does not use a real data value of collected biometric information in an authentication procedure so as to inhibit a damage if the biometric information is leaked, and performs the authentication procedure by using only a figure or a form of a graph indicating a variation in a specific section or by using a data arithmetic value obtained by performing a predetermined arithmetic operation with respect to the real data value, and an authentication method using the same.

Technical Solution

According to an embodiment of the present disclosure to achieve the above-described object, a variable biometric information-based authentication system includes: a mobile terminal configured to generate information regarding an ID that intends to access a facility or information requiring an access authority, and to collect variable biometric information, such that information regarding the ID and the variable biometric information are stored all together; and a variable biometric information management server configured to, when the mobile terminal requests a login command regarding the ID, verify validity of the login command regarding the ID based on the variable biometric information.

Herein, the variable biometric information management server may be configured to determine whether the specific ID is an ID of a first security level or an ID of a second security level based on the information regarding the ID. The ID of the first security level may allow the validity of the login command regarding the ID to be verified based on one type of variable biometric information, and the ID of the second security level may allow the validity of the login command regarding the ID to be verified based on a combination of two or more types of variable biometric information or a complex arithmetic relation.

When the specific ID is the ID of the first security level, the mobile terminal may be configured to collect the variable biometric information, and to transmit only information regarding a figure or a form of a graph indicating a variation in a specific section, without transmitting a real value of the collected variable biometric information to the variable biometric information management server.

In addition, the variable biometric information management server may be configured to: when the information regarding the ID matched with the variable biometric information and stored, and the variable biometric information including only the information regarding the figure or the form of the graph are received, store the received information regarding the ID and the variable biometric information; when a login command regarding the specific ID is requested, receive variable biometric information for verifying validity of the login command from the mobile terminal; and compare the received variable biometric information and the figure or the form of the graph included in the stored variable biometric information including only the information regarding the figure or the form of the graph on a real time basis, and to verify the validity of the login command.

In addition, the variable biometric information management server may be configured to accumulate and store the variable biometric information including only the figure or the form of the graph according to the information regarding the ID, and, when the mobile terminal requests the variable biometric information stored for the specific ID to be discarded, the variable biometric information management server may be configured to discard the variable biometric information stored for the specific ID, and to accumulate and store the variable biometric information transmitted with the information regarding the specific ID after the stored variable biometric information is discarded, according to the information regarding the ID.

In addition, when the specific ID is the ID of the first security level, the mobile terminal may be configured to collect and store the variable biometric information in the unit of a predetermined time, and to add information regarding time to the variable biometric information and to store the information, and the mobile terminal may be configured to transmit the information regarding the time and the information regarding the figure or the form of the graph indicating the variation in the specific section, without transmitting the real value of the collected variable biometric information to the variable biometric information management server.

In addition, when the login command regarding the ID is requested, the variable biometric information management server may be configured to compare information regarding time, added to variable biometric information received from the mobile terminal, and the information regarding the time, added to the variable biometric information received from the variable biometric information management server, and to determine equivalence therebetween, and, when it is determined the respective pieces of information regarding the times are equal to each other, the variable biometric information management server may be configured to determine equivalence between the respective pieces of variable biometric information, and to verify the validity of the login command regarding the ID.

In addition, when the specific ID is the ID of the second security level, the mobile terminal may be configured to collect the two or more types of variable biometric information, and to match respective pieces of classification information with the information regarding the ID, such that the respective types of variable biometric information are identified.

In addition, when the specific ID is the ID of the second security level, the variable biometric information management server may be configured to receive, from the mobile terminal, first variable biometric information and second variable biometric information in which different types of classification information are matched with the information regarding the ID, and to store the first and second variable biometric information, and, when the login command regarding the ID is requested, the variable biometric information management server may be configured to receive first variable biometric information and second variable biometric information matched with information regarding the ID requesting the login command from the mobile terminal, and to individually determine whether the stored first variable biometric information and second variable biometric information are equal to the received first variable biometric information and second variable biometric information, and to verify the validity of the login command regarding the ID.

In addition, when the mobile terminal is connected to a short range communication network, the mobile terminal may be configured to transmit the stored variable biometric information to the variable biometric information management server at predetermined time intervals.

In addition, the variable biometric information may include one or more pieces of information from among user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces.

In addition, according to another embodiment of the present disclosure to achieve the above-described object, a variable biometric information-based authentication system includes: a plurality of mobile terminals configured to generate information regarding an ID that intends to access a facility or information requiring an access authority, and to collect variable biometric information, such that information regarding the ID and the variable biometric information are stored all together; and a variable biometric information management server configured to receive the information regarding the ID and the variable biometric information from the plurality of mobile terminals, and to store the information; and an agent server configured to, when the mobile terminal request a login command regarding the ID, compare the variable biometric information received from the variable biometric information management server and variable biometric information received from the mobile terminal, and to verify validity of the login command regarding the ID.

According to an embodiment of the present disclosure to achieve the above-described object, a variable biometric information-based authentication method includes the steps of: generating, by a mobile terminal, information regarding an ID that intends to access a facility or information requiring an access authority, and collecting variable biometric information; storing the information regarding the ID and the variable biometric information, received from the mobile terminal, in a variable biometric information management server all together; and, when the mobile terminal requests a login command regarding the ID, verifying, by the variable biometric information management server, validity of the login command regarding the ID based on the variable biometric information.

Advantageous Effects

Accordingly, a real data value of collected biometric information is not used in the authentication procedure, and the authentication procedure is performed only by using a figure or a form of a graph indicating a variation in a specific section or a data arithmetic value obtained by performing a predetermined arithmetic operation with respect to the real data value. Therefore, even if the biometric information used in the authentication procedure is leaked, a damage resulting therefrom can be inhibited.

In addition, since a security level of the authentication procedure can be selectively determined, the security of the authentication procedure can be enhanced by combining different types of variable biometric information or by combining variable biometric information of a plurality of users. In addition, as the security level of the authentication procedure is selectively determined, the authentication procedure can be diversely utilized in an entering authentication to a facility such as an office or school or secure authentication in financial services such as account transfer, payment, etc.

In addition, the result of the entering authentication to the facility may be stored and may be utilized for management of absenteeism and tardiness of a company or management of school attendance.

BEST MODE

Hereinafter, the present disclosure will be described in more detail with reference to the accompanying drawings. Exemplary embodiments introduced hereinafter are provided such that the idea of the present disclosure is fully conveyed to a person skilled in the art. The present disclosure is not limited to embodiments described below and may be specified in other forms.

Figure 1:
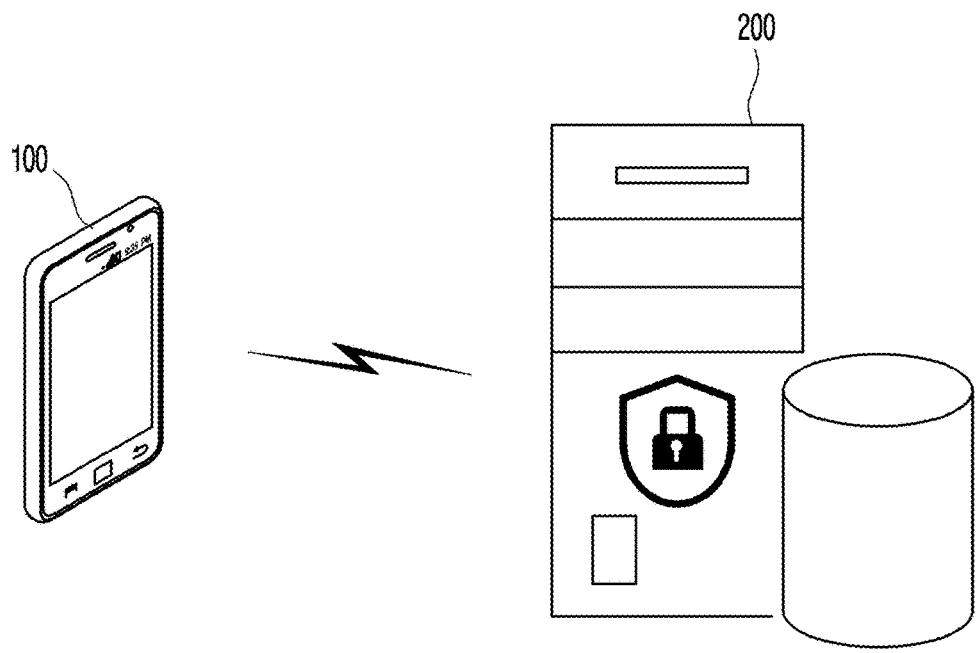
FIG. 1 is a view schematically showing a variable biometric information-based authentication system according to an embodiment of the present disclosure.
Figure 2:
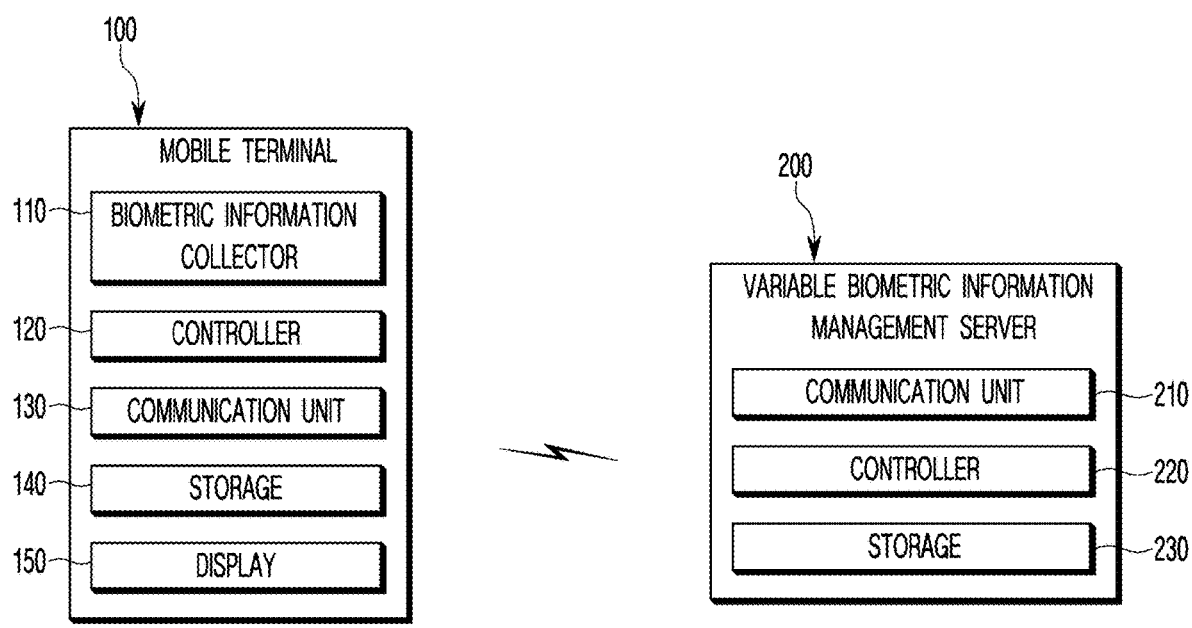
FIG. 2 is a block diagram provided to illustrate a configuration of a variable biometric information-based authentication system according to an embodiment of the present disclosure.

FIG. 1 is a view schematically showing a variable biometric information-based authentication system according to an embodiment of the present disclosure, and FIG. 2 is a block diagram provided to illustrate a configuration of a variable biometric information-based authentication system according to an embodiment of the present disclosure.

Hereinafter, a variable biometric information-based authentication system (hereinafter, referred to as an "authentication system") according to an embodiment will be described with reference to FIGS. 1 and 2.

The authentication system according to an embodiment may selectively determine a security level of an authentication procedure, and may be provided to perform the authentication procedure using personal variable biometric information, which changes according to times and environments, so as to inhibit a damage even if the biometric information used in the authentication procedure is leaked.

To achieve this, the authentication system may include a mobile terminal 100 and a variable biometric information management server 200.

Specifically, the mobile terminal 100 may be implemented by using a device such as a smart phone or a smart watch, and may collect and store biometric information, such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces, or may transmit the collected variable biometric information to the variable biometric information management server 200.

In addition, the mobile terminal 100 may generate information regarding an ID that intends to access a facility or information requiring an access authority, and may match the information regarding the ID and the collected variable biometric information, and may store the matched information.

To achieve this, the mobile terminal 100 includes a biometric information collector 110, a controller 120, a communication unit 130, a storage 140, and a display 150.

The biometric information collector 110 of the mobile terminal is provided to collect variable biometric information.

Specifically, the biometric information collector 110 may be provided inside the mobile terminal 100 or may be provided outside the mobile terminal, like a smart scale, a smart blood pressure gauge, a smart blood glucose monitor, a smart watch, a smart band, and a smart insole, to interwork with the mobile terminal 100, and may collect biometric information such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces, In this case, the mobile terminal 100 may be provided with a plurality of biometric information collectors 110 to collect various types of biometric information.

The controller 120 of the mobile terminal is provided to control elements of the mobile terminal 100 and to perform overall tasks of the mobile terminal 100.

Specifically, the controller 120 may generate information regarding an ID that intends to access a facility or information requiring an access authority, and may match variable biometric information collected by the biometric information collector 110 with the information regarding the ID, and may store the matched information in the storage 140 or may transmit the matched information to the biometric information management server 200 via the communication unit 130.

However, the variable biometric information includes sensitive information related to user's personal information, diseases or health state, and thus, when such information is leaked, there may be concern about a damage caused by an illegal use of a password, and also, a more serious damage may be caused by personal information leakage.

Accordingly, the controller 120 may collect variable biometric information, but may not transmit a real value of the collected variable biometric information to the variable biometric information management server 200. Instead, the controller 120 may transmit only information regarding a figure or a form of a graph indicating a variation in a specific section along with the information regarding the ID. Therefore, even when the variable biometric information transmitted to the variable biometric information management server 200 is leaked, a damage resulting therefrom can be minimized or inhibited.

In another example, the controller 120 may store the collected variable biometric information in the unit of a predetermined time, and may add information regarding time to the variable biometric information and store the information.

By doing so, the controller 120 may identify the collected plurality of pieces of variable biometric information according to collection times. Afterward, in the process of comparing variable biometric information stored in the variable biometric information management server 200 and variable biometric information stored in the mobile terminal 100 to verify validity of a login command, the variable biometric information management server 200 may compare only pieces of variable biometric information added with information regarding the same time each other, such that time required to verify can be reduced and verification reliability can be enhanced.

That is, when a login command regarding an ID is requested, the variable biometric information management server 200 may compare information regarding time, added to variable biometric information received from the mobile terminal 100, and information regarding time stored therein, and may determine equivalence therebetween, and, when it is determined that two pieces of information regarding time are equal to each other, the variable biometric information management server 200 may verify validity of the login command regarding the ID by determining whether stored variable biometric information and variable biometric information received after the login command is requested are equal to each other.

In addition, the controller 120 may generate information regarding an ID that intends to access a facility or information requiring an access authority, and may access the variable biometric information management server 200 and register an ID that can identify whose biometric information the variable biometric information is.

Specifically, for example, the controller 120 may register a plurality of IDs at the variable biometric information management server 200, and, even when the plurality of IDs are registered at the variable biometric information management information 200, the controller 120 may designate one ID, and may match information regarding the designated ID and variable biometric information and transmit the matched information.

In addition, when the mobile terminal 100 is connected to a short range communication network, the controller 120 may control to transmit the variable biometric information stored in the storage 140 to the variable biometric information management server 200 at predetermined time intervals.

By doing so, stored existing variable biometric information may be replaced with newly collected variable biometric information and may be updated, and, even when biometric information used in the authentication procedure is leaked, a damage resulting therefrom can be inhibited.

The communication unit 130 of the mobile terminal is provided to access the variable biometric information management server 200 or other external servers using the communication network to perform Internet communication.

Specifically, the communication unit 130 may transmit a login command regarding a specific ID to the variable biometric information management server 200, or may transmit collected variable biometric information to the variable biometric information management server 200.

The storage 140 of the mobile terminal is provided to store applications and data necessary for performing the tasks of the mobile terminal 100.

Specifically, the storage 140 may match information regarding an ID and variable biometric information, and may store the matched information.

In addition, the storage 140 may match information regarding an ID and variable biometric information, and may add information regarding time and store the information. In this case, the variable biometric information may be stored in the unit of a predetermined time.

Herein, the information regarding the time is information regarding a time at which variable biometric information is collected, and, when variable biometric information is expressed by a graph indicating a variation of a real value according to time, the variable biometric information may be expressed by graphs of various forms according to a time unit, and thus the information regarding the time may be an important factor in comparing variable biometric information.

The display 150 of the mobile terminal is provided to output information that the mobile terminal 100 intends to output.

In addition, the mobile terminal 100 may be provided with an input unit (not shown) to input a command related to a task to perform, and a battery unit (not shown) to supply power, in addition to the controller 120, the communication unit 130, the storage 140, and the display 150 described above.

The variable biometric information management server 200 may manage variable biometric information received from the mobile terminal 100, and, when the mobile terminal 100 requests a login command using a specific ID that intends to access a facility or a host computer requiring an access authority, or information stored in a network, the variable biometric information management server 200 may verify validity of the requested login command, and, when it is determined that the login command is valid, the variable biometric information management server 200 is provided to give an authority to access the facility or host computer requiring the access authority, or the information stored in the network.

Specifically, when information regarding an ID and collected variable biometric information are received, the variable biometric information management server 200 may store the received variable biometric information and the information regarding the ID, already registered by the mobile terminal 100, and, when the mobile terminal 100 requests a login command using a specific ID that intends to access a facility or a host computer requiring an access authority, or information stored in a network, the variable biometric information management server 200 may receive variable biometric information from the mobile terminal 100, and may verify validity of the requested login command by comparing the received variable biometric information and the stored variable biometric information.

To achieve this, the variable biometric information management server 200 includes a communication unit 210, a controller 220, and a storage 230.

The communication unit 210 of the variable biometric information management server is provided to be connected with the mobile terminal 100 using a communication network and to perform Internet communication.

Specifically, the communication unit 210 may receive variable biometric information from the mobile terminal 100 and store the same, and then, when a login command regarding a specific ID is requested by the mobile terminal 100, the communication unit 210 may receive variable biometric information from the mobile terminal 100.

The controller 220 of the variable biometric information management server is provided to control elements of the variable biometric information management server 200 and to perform overall tasks of the variable biometric information management server 200.

Specifically, the controller 220 may register an ID for identifying whose biometric information the variable biometric information is according to a request of the mobile terminal 100, and may receive information regarding the registered ID via the communication unit.

Herein, the ID refers to an ID of a user account that can identify whose biometric information the variable biometric information is, and also, is used for the user to access a facility or information requiring an access authority via the variable biometric information management server 200. When the ID is registered, the controller 220 may determine whether the ID is an ID of a first security level that allows validity of a login command to be verified based on one type of variable biometric information, or an ID of a second security level that allows validity of a login command to be verified based on two or more types of variable biometric information.

Accordingly, when a login command regarding a specific ID is requested, the controller 220 may determine whether the corresponding ID is the ID of the first security level or the ID of the second security level, and may verify validity of the login command.

In addition, when information regarding an ID and variable biometric information are received via the communication unit 210, the controller 220 may control to store the received information regarding the ID and the received variable biometric information.

In addition, the controller 220 may compare variable biometric information matched with information regarding an ID and stored, and variable biometric information received from the mobile terminal 100 to verify validity of a login command regarding a specific ID according to a request of the mobile terminal 100.

For example, the controller 220 may compare the variable biometric information matched with the information regarding the ID and stored, and the variable biometric information received from the mobile terminal, but, in this case, the controller 220 may compare only information regarding a figure or a form of a graph indicating a variation in a specific section, and may verify the validity of the login command regarding the specific ID according to equivalence between two pieces of information.

In another example, the controller 220 may compare the variable biometric information matched with the information regarding the ID and stored, and the variable biometric information received from the mobile terminal, but, in this case, the controller 220 may select only variable biometric information in a specific section or variable biometric information at a specific time and may compare the same, or may compare an average value of the variable biometric information matched with the information regarding the ID and stored, and an average value of the variable biometric information received from the mobile terminal, and may verify the validity of the login command regarding the specific ID according to equivalence between two pieces of information.

The storage 230 of the variable biometric information management server is provided to store programs and data necessary for performing tasks of the variable biometric information management server 200.

Specifically, the storage 230 may store variable biometric information matched with information regarding an ID, which is received from the mobile terminal 100.

Additionally, the mobile terminal 100, which is an element of the authentication system of the present disclosure, may be substituted with a computer (PC) provided with a means for collecting variable biometric information, such as a smart scale, a smart blood pressure gauge, a smart blood glucose monitor, a smart watch, a smart band, and a smart shoe insole.

Furthermore, the above-mentioned biometric information is an example of biometric information which variably changes according to a user's emotion state, health state, time, temperature, or other external environments, rather than being information which permanently unchanges with respect to a specific user, and biometric information that has not been mentioned above can be applied to the present disclosure if it variably changes.

Figure 3:
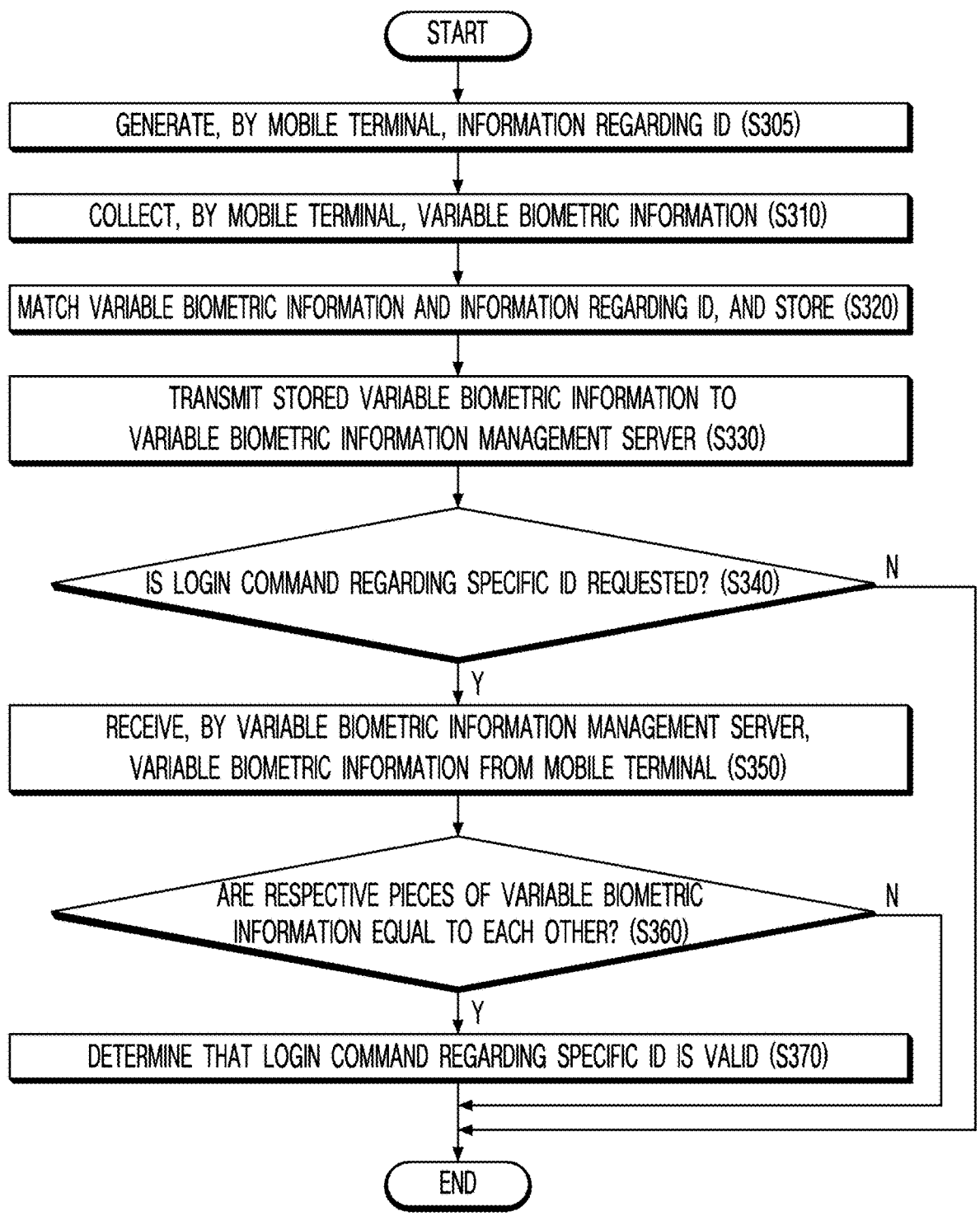
FIG. 3 is a flowchart provided to illustrate a variable biometric information-based authentication method according to an embodiment of the present disclosure.
Figure 4:
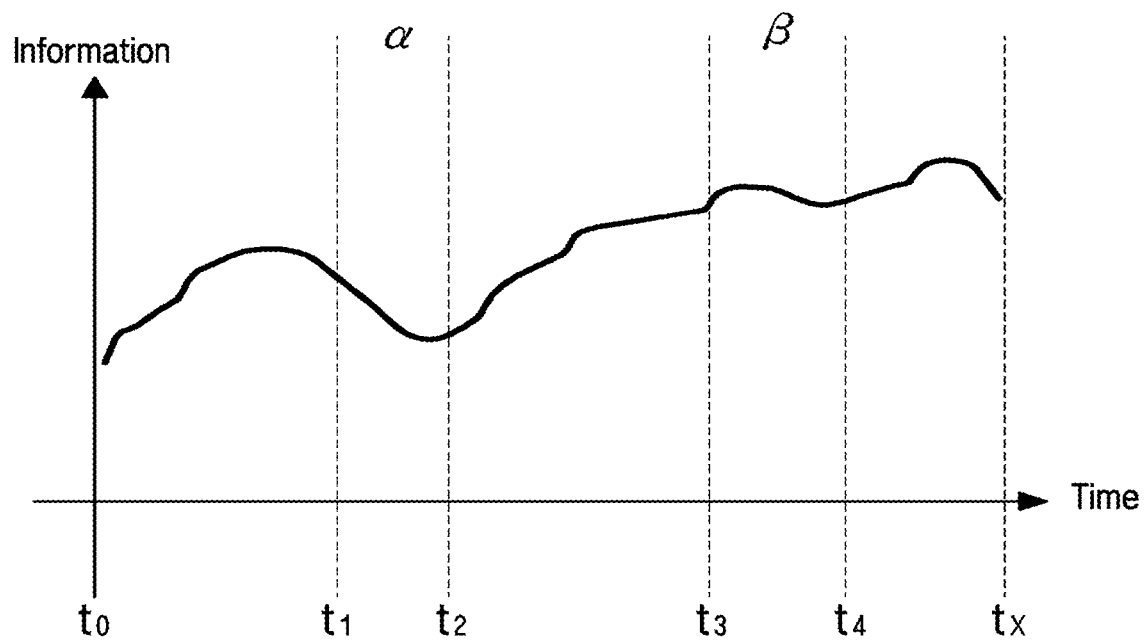
FIG. 4 is a view provided to illustrate variable biometric information which is collected and stored according to a variable biometric information-based authentication method according to an embodiment of the present disclosure.
Figure 5:
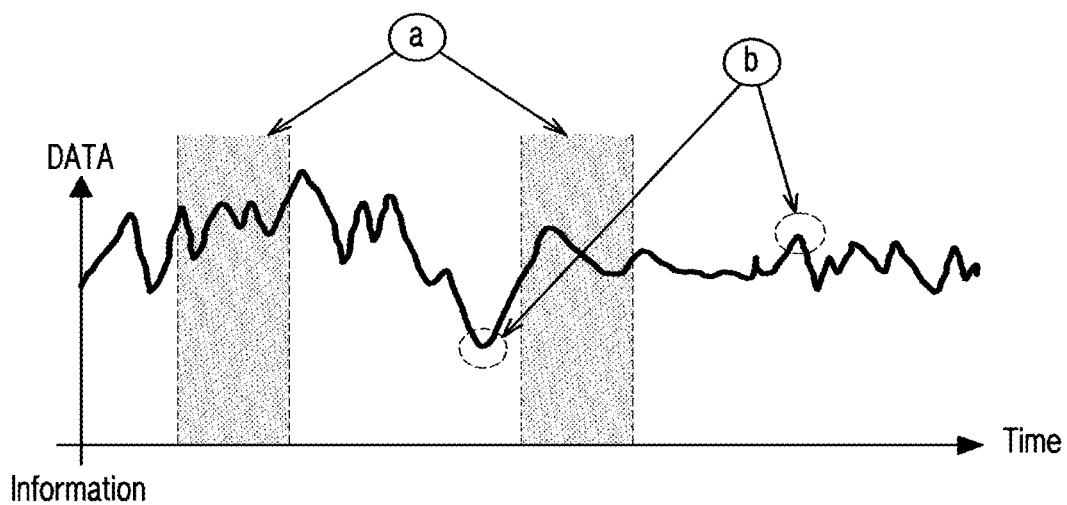
FIG. 5 is a view provided to illustrate a process of determining equivalence between variable biometric information according to a variable biometric information-based authentication method according to an embodiment of the present disclosure.
Figure 6:
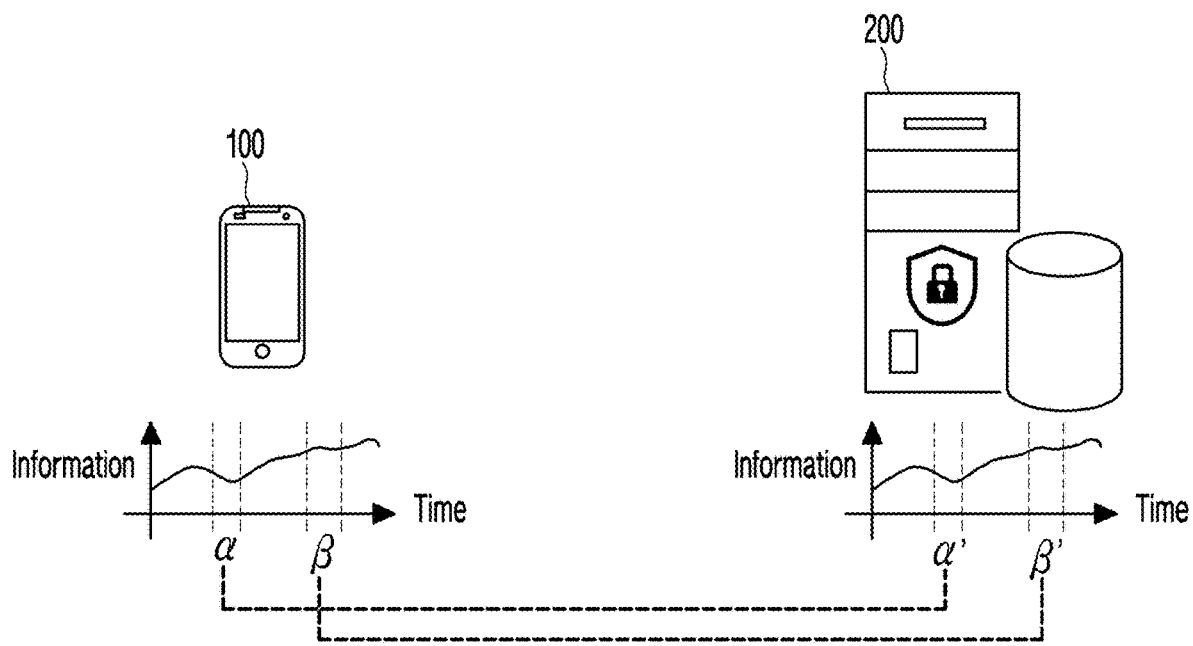
FIG. 6 is a view provided to illustrate a process of determining equivalence between variable biometric information according to a variable biometric information-based authentication method according to an embodiment of the present disclosure.

FIG. 3 is a flowchart provided to illustrate a variable biometric information-based authentication method according to an embodiment of the present disclosure, FIG. 4 is a view provided to illustrate variable biometric information which is collected and stored according to a variable biometric information-based authentication method according to an embodiment of the present disclosure, and FIGS. 5 and 6 are views provided to illustrate variable biometric information which is collected and stored according to a variable biometric information-based authentication method according to an embodiment of the present disclosure.

Hereinafter, a variable biometric information-based authentication method (hereinafter, referred to as an "authentication method") according to an embodiment will be described with reference to FIGS. 3 to 6.

The authentication method according to an embodiment does not use a real data value of collected biometric information in an authentication procedure, and performs the authentication procedure only using a figure or a form of a graph indicating a variation in a specific section so as to inhibit a damage even if information is leaked by using the above-described authentication system.

First, the mobile terminal 100 may generate information regarding an ID that intends to access a facility or information requiring an access authority (S305), and, when variable biometric information is collected (S310), the mobile terminal 100 may match the generated information regarding the ID and the variable biometric information each other, and store the matched information (S320).

In addition, the mobile terminal 100 may transmit the stored variable biometric information to the variable biometric information management server 200 (S330).

In briefly describing the variable biometric information, the variable biometric information may have a value corresponding time. When data of predetermined information is collected, the data may be outputted in the form of a figure or a graph indicating a variation in a specific section as shown in FIG. 4.

For example, the mobile terminal 100 may collect variable biometric information that can be outputted in the form of a graph, and may store the collected variable biometric information in the unit of a predetermined time, and may add information regarding time to the variable biometric information and store the variable biometric information.

In this case, however, the form of the graph may be variously expressed according to a value of time and a value of information which are reflected on the graph.

Specifically, when a time interval reflected on the graph with respect to specific variable biometric information is set to hours or minutes, the same variable biometric information may be expressed by a graph of a gentle slope or a graph of a steep slope according to a set time interval. Accordingly, the variable biometric information may be diversely utilized according to an analysis method.

For example, with respect to variable biometric information to which a specific time, rather than seconds or minutes, should be applied like blood pressure, equivalence between information may be determined by comparing graph information which changes with time. With respect to such variable biometric information, outputting a graph showing a value of information of a specific time (for example, 8 o'clock a.m.) makes it easier to determine equivalence between information than outputting a graph showing data at time intervals of seconds or minutes like a body fat percentage or abdominal visceral fat.

In addition, such variable biometric information includes sensitive information related to user's personal information, diseases, or health state, and thus, when such information is leaked, there may be concern about a damage caused by an illegal use of a password, and also, a more serious damage may be caused by personal information leakage.

Accordingly, the mobile terminal 100 may collect variable biometric information, but may not transmit a real value of the collected variable biometric information to the variable biometric information management server 200, and may transmit only information regarding a figure or a form of a graph indicating a variation in a specific section, along with information regarding an ID. Therefore, even when the variable biometric information transmitted to the variable biometric information management server 200 is leaked, a damage resulting therefrom can be minimized or inhibited.

In addition, the variable biometric information management server 200 may accumulate and store the variable biometric information including only the information regarding the figure or the form of the graph according to the information regarding the ID. However, when the mobile terminal requests to discard variable biometric information stored for a specific ID, the variable biometric information management server 200 may discard the variable biometric information stored for the specific ID.

In addition, the variable biometric information management server 200 may accumulate and store variable biometric information, transmitted along with information regarding a specific ID after the stored variable biometric information is discarded, according to the information regarding the ID.

In addition, the method for outputting the variable biometric information in the form of a figure or a graph indicating a variation in a specific section may be diversely applied. A width of a section and setting information of the section, which influence the form of the graph, may be diversely set by considering user's setting, type of biometric information, a collection period and a collection time, physiological characteristics of biometric information. Since collected data is also recorded with numerical values, the data may be expressed by graphs of various forms by adjusting specific values of the information and the time. Accordingly, even with respect to biometric information having a small variation, it is possible to make a visual form of data like a specific figure or a form or pattern of a graph.

For example, even when a body fat percentage minimally changes from 19% to 19.2%, morphological changes may appear in a graph according to whether data is expressed by the graph in the unit of 10% or 1%. Therefore, the data can be utilized as a figure, a form of a graph, or pattern data for being utilized in personal identification and authentication.

For example, referring to FIG. 4, the mobile terminal 100 may set times from t0 to tx to a time unit, and may collect and store variable biometric information corresponding to values corresponding to times t0 to tx, and may add information regarding time to the variable biometric information and store the information.

However, as the information regarding the time, information regarding times t1 to t2 and information regarding times t3 to t4 may be individually generated. Therefore, even if variable biometric information is stored in one time unit, information regarding a specific time may be identified and may assist in enhancing accuracy of the authentication procedure.

The accuracy of the authentication procedure will be described in more detail with description of a procedure of verifying validity of a login command.

When the mobile terminal 100 requests a login command regarding a specific ID after transmitting information regarding an ID and variable biometric information to the variable biometric information management server 200, the variable biometric information management server 200 receives variable biometric information from the mobile terminal 100.

Specifically, when a login command regarding a specific ID is requested, the variable biometric information management server 200 may request variable biometric information from the mobile terminal 100.

In another example, the variable biometric information management server 200 may be configured to request a login command regarding a specific ID only when the mobile terminal 100 transmits variable biometric information regarding the specific ID that intends to request the login command. Therefore, when a user who does not have a valid authority recklessly requests a login command regarding the specific ID, a burden to the variable biometric information management server 200 in processing data can be reduced.

When the variable biometric information is received from the mobile terminal 100, the variable biometric information management server 200 compares the received variable biometric information and the variable biometric information matched with the information regarding the specific ID (S360), and may verify validity of the login command regarding the specific ID (S370).

Specifically, the variable biometric information management server 200 may compare a figure or a form of a graph of the variable biometric information, matched with the information regarding the specific ID and stored, and a figure or a form of a graph of the variable biometric information, received from the mobile terminal 100 after the login command is requested, on a real time basis. In this case, the variable biometric information management server 200 may compare information regarding time, added to the variable biometric information matched with the information regarding the specific ID and stored, and information regarding time, added to the variable biometric information received from the mobile terminal 100, and may determine equivalence therebetween. When it is determined that the respective pieces of time information are equal to each other, the variable biometric information management server 200 may verify the validity of the login command regarding the specific ID by determining equivalence between the respective pieces of variable biometric information.

For example, as shown in FIG. 6, the variable biometric information management server 200 may compare information ($\alpha$) regarding time, added to variable biometric information received from the mobile terminal 100, and pieces of information ($\alpha'$ and $\beta'$) regarding times, added to variable biometric information stored in the variable biometric information management server 200, and may determine equivalence therebetween. When it is determined that there exists information ($\alpha'$) regarding the same time, the variable biometric information management server 200 may compare figures or forms of graphs of the variable biometric information to which the information ($\alpha'$) regarding the same time is added, and may determine equivalence therebetween.

In addition, the variable biometric information management server 200 may determine equivalence between pieces of variable biometric information to which information regarding one same time is added, and also, may individually determine equivalence with respect to pieces of information regarding two or more times and may complexly process the results of determining equivalence.

Specifically, the variable biometric information management server 200 may compare variable biometric information to which information ($\alpha$) regarding a first time is added, and variable biometric information to which information ($\alpha'$) regarding the same time as the information ($\alpha$) regarding the first time is added, and may determine equivalence therebetween, and may compare variable biometric information to which information ($\beta$) regarding a second time is added, and variable biometric information to which information ($\beta'$) regarding the same time as the information ($\beta$) regarding the second time is added, and may determine equivalence therebetween. In this case, only when all of the results of determining equivalence indicate equivalence, the validity of the login command regarding the specific ID may be recognized.

In addition to the respective results of determining equivalence, the variable biometric information management server 200 may diversely set an average of the variable biometric information to which the information ($\alpha$) regarding the first time is added, and the variable biometric information to which the information ($\beta$) regarding the second time is added, or a complex arithmetic relation between two pieces of variable biometric information, and may compare the two pieces of variable biometric information.

For example, a sum value, a subtraction value, a multiplication value, or an average value regarding data of average weight 70.5 kg of October in 2016 and data of average weight of 71.5 kg of December in 2016 may be calculated, and equivalence between variable biometric information may be determined although direct numerical values of the variable biometric information are not compared.

In addition, when the mobile terminal transmits a real value of variable biometric information, the variable biometric information management server 200 may encrypt an information value of the variable biometric information to which the information ($\alpha$) regarding the first time is added, and an information value of the variable biometric information to which the information ($\beta$) regarding the second time is added, so as to inhibit a damage caused by the leakage of the variable biometric information, and then may determine equivalence therebetween, and may verify the validity of the login command regarding the specific ID.

In particular, when the variable biometric information to which the information ($\alpha$) regarding the first time is added, and the variable biometric information to which the information ($\beta$) regarding the second time is added are encrypted, the identification information corresponding to the specific ID, matched with the variable biometric information, and the information regarding the time may be utilized as a key value of a seed key for encryption, such that the same identification information is matched with the information regarding the time. In addition, regarding the pieces of variable biometric information to which the information regarding the same time is added, equivalence therebetween may be determined even after they are encrypted. Therefore, a damage by the leakage of biometric information can be minimized and the validity of the login command regarding the specific ID can be verified.

However, when the pieces of variable biometric information to which the information regarding the same time is added are compared with each other, the variable biometric information may be outputted in the form of a pattern (a) of information values during a specific time interval, or in the form of an information value (b) at a specific time, as shown FIG. 5.

In this case, according to the pattern (a) of the information values during the specific time interval, equivalence between the variable biometric information may be determined based on a graph outputting a specific change value according to the contraction and expanding of the heart during the specific time interval, like an electrocardiogram (ECG) graph.

Figure 7:
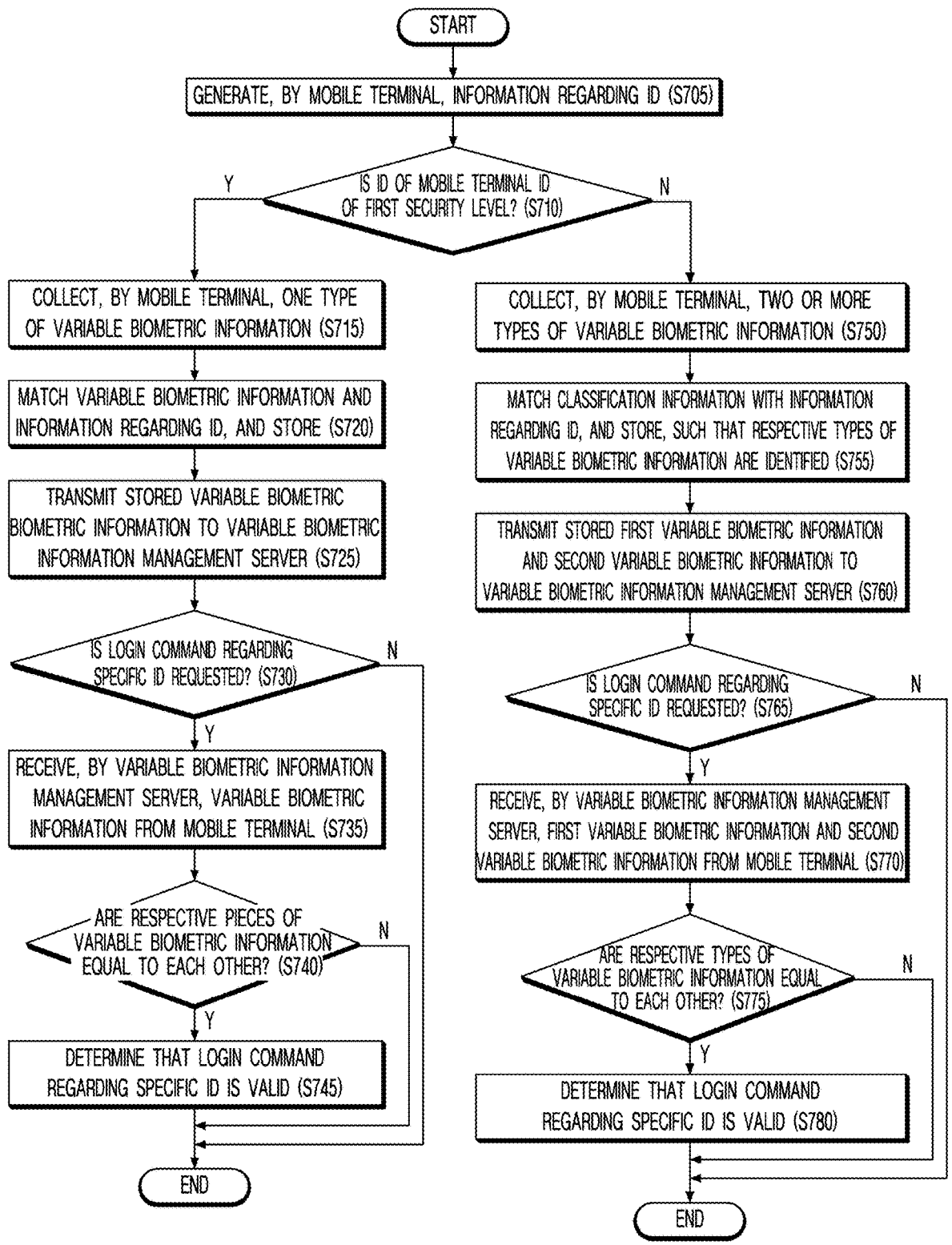
FIG. 7 is a flowchart provided to illustrate a variable biometric information-based authentication method in detail according to an embodiment of the present disclosure.
Figure 8:
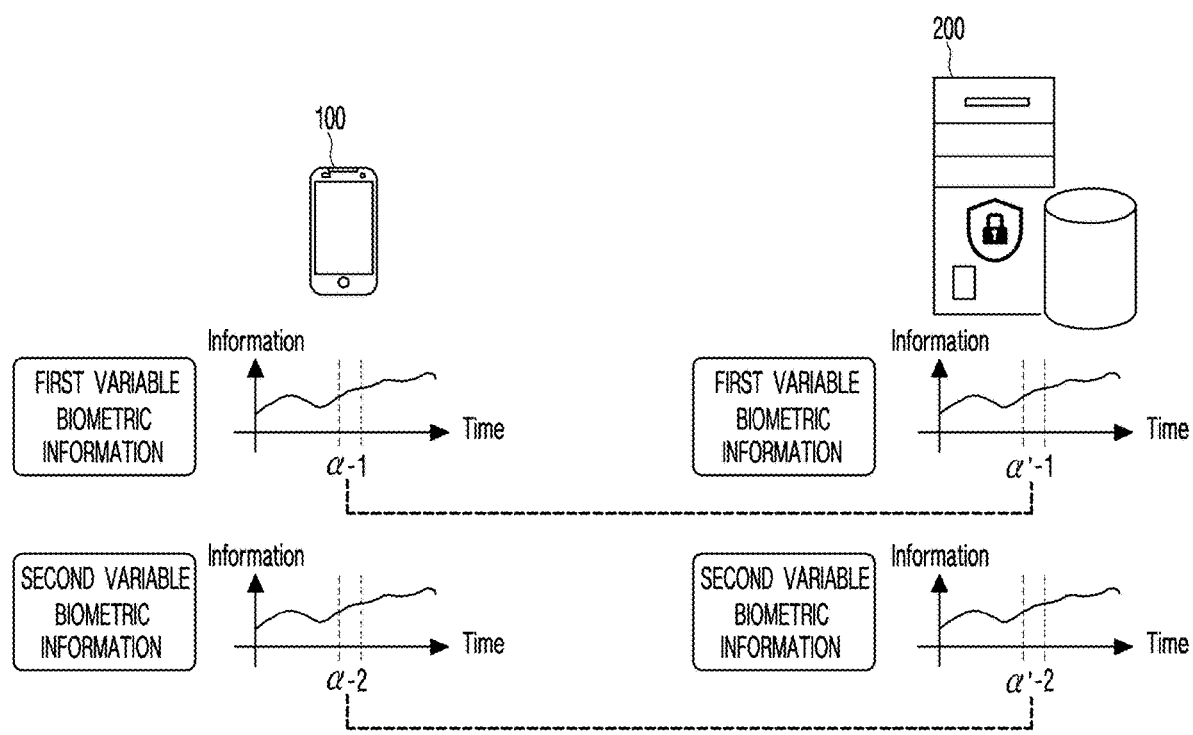
FIG. 8 is a view provided to illustrate a process of determining equivalence between variable biometric information according to a variable biometric information-based authentication method according to an embodiment of the present disclosure.
Figure 9:
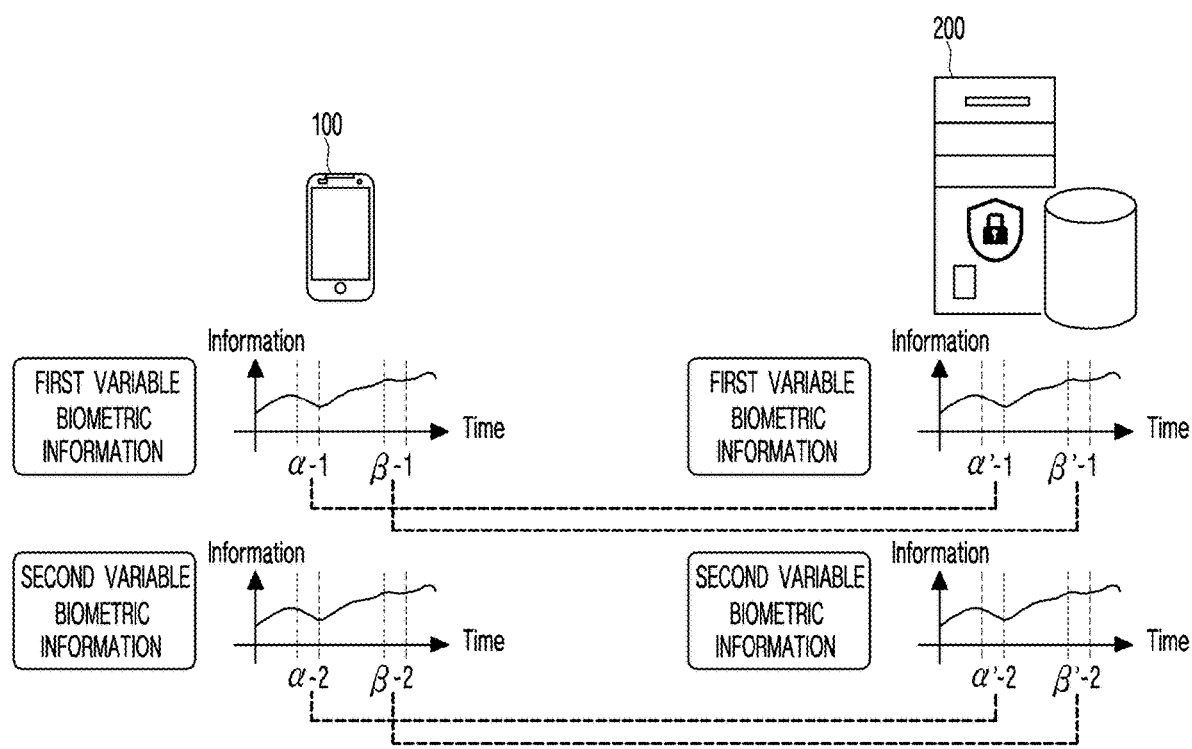
FIG. 9 is a view provided to illustrate a process of determining equivalence between variable biometric information according to a variable biometric information-based authentication method according to an embodiment of the present disclosure.

FIG. 7 is a flowchart provided to illustrate a variable biometric information-based authentication method in more detail according to an embodiment of the present disclosure. FIGS. 8 and 9 are views provided to illustrate a process of determining equivalence between variable biometric information according to the variable biometric information-based authentication method according to an embodiment of the present disclosure.

Hereinafter, the authentication method according to an embodiment will be described in more detail, but a redundant explanation will be omitted.

According to the authentication method according to an embodiment, when the mobile terminal 110 generates information regarding an ID that intends to access a facility or information requiring an access authority, and transmits the information regarding the ID (S705), the variable biometric information management server 200 may determine a security level of the specific ID based on the received ID information (S710).

Specifically, the variable biometric information management server 200 may determine whether the specific ID is an ID of a first security level (S710-Y) or an ID of a second security level (S710-N) based on the received ID information. Herein, in the case of the ID of the first security level, validity of a login command regarding the ID may be verified based on one type of variable biometric information, and, in the case of the ID of the second security level, validity of a login command regarding the ID may be verified based on a combination of two or more types of variable biometric information or based on a complex arithmetic relation.

In this case, when the specific ID is the ID of the first security level (S710-Y), the mobile terminal 100 may collect one type of variable biometric information (S715), and may match the information regarding the ID and one type of variable biometric information and may store the matched information (S720).

Specifically, when the specific ID is the ID of the first security level (S710-Y), the mobile terminal 100 may collect one type of variable biometric information and may match the same with the information regarding the ID. In this case, however, the mobile terminal 100 may not transmit a real value of the collected variable biometric information to the variable biometric information management server 200, and may match only information regarding a figure or a form of a graph indicating a variation in a specific section, with the information regarding the ID, and may transmit the matched information to the variable biometric information management server 200.

However, data stored in the mobile terminal 100 may be data including all of the real values of the variable biometric information. In this case, the variable biometric information may be matched with the information regarding the ID and stored, and only the information regarding the figure or the form of the graph may be extracted from the real values of the variable biometric information prior to being transmitted to the variable biometric information management server, and may be transmitted along with the information regarding the ID.

In another example, when the specific ID is the ID of the first security level (S710-Y), the mobile terminal 100 may collect and store variable biometric information in the unit of a predetermined time, and also may add information regarding time to respective pieces of variable biometric information and store the same.

In this case, the mobile terminal 100 may also not transmit the real values of the collected variable biometric information to the variable biometric information management server 200, and may transmit only information regarding a figure or a form of a graph indicating a variation in a specific section, along with the information regarding the time.

In addition, when the variable biometric information and the information regarding the ID are matched with each other and stored, the mobile terminal 100 may transmit the stored variable biometric information to the variable biometric information management server 200 (S725).

When the mobile terminal 100 requests a login command regarding a specific ID after transmitting the information regarding the ID and the variable biometric information to the variable biometric information management server 200 (S730-Y), the variable biometric information management server 200 may receive variable biometric information from the mobile terminal 100 (S735).

When the variable biometric information is received from the mobile terminal 100, the variable biometric information management server 200 may compare the received variable biometric information and the variable biometric information matched with the information regarding the specific ID (S740), and may verify validity of the login command regarding the specific ID (S745).

However, when the information regarding the ID generated by the mobile terminal 100 and the collected variable biometric information are transmitted to the variable biometric information management server 200, the security level of the corresponding ID may be determined after the biometric information is collected, and, even when two or more types of variable biometric information are collected by the mobile terminal, the variable biometric information transmitted along with the information regarding the ID of the first security level may be one type of variable biometric information.

Accordingly, the mobile terminal may generate the information regarding the ID, and may match the generated ID and collected biometric information with each other rather than collecting biometric information according to the generated ID, such that the collected biometric information can perform a role of a password to be used for the authentication procedure. In this case, if it can be verified whether the authentication procedure is valid not by comparing the real values of the collected variable biometric information, but by comparing figures or forms of graphs visually expressed in the same condition (intervals in the graph indicating time or real values), a time at which the information regarding the ID is generated the security level of the generated ID is generated, and a time at which the biometric information is collected may be diversely changed according to the technical idea of the present disclosure and may be utilized.

On the other hand, when the specific ID is the ID of the second security level (S710-N), the mobile terminal 100 may collect two or more types of variable biometric information (S750), and may match the variable biometric information and the information regarding the ID (S755). In this case, however, the mobile terminal 100 may not transmit the real values of the collected variable biometric information to the variable biometric information management server 200, and may match only information regarding a figure of a form of a graph indicating a variation in a specific section with the information regarding the ID, and may transmit the matched information to the variable biometric information management server 200 (S760).

Specifically, when the specific ID is the ID of the second security level (S710-N), the mobile terminal 100 may collect two or more types of variable biometric information (S750), and may match respective pieces of classification information with the information regarding the ID and the respective pieces of variable biometric information, such that the respective types of variable biometric information can be identified (S755).

For example, when two types of variable biometric information are collected as shown in FIG. 8, one type of variable biometric information is referred to as first variable biometric information, and the other type of variable biometric information is referred to as second variable biometric information. In this case, the mobile terminal 100 may match respective pieces of classification information and the information regarding the specific ID with the first variable biometric information and the second variable biometric information, and may transmit the matched information to the variable biometric information management server 200 (S760)

In this case, the transmitted variable biometric information may not include real values of the variable biometric information, and may include only information regarding a figure or a form of a graph indicating a variation in a specific section.

In addition, when a login command regarding a specific ID is requested (S765-Y) after the first variable biometric information and the second variable biometric information, matched with the classification information and the information regarding the specific ID, are transmitted and stored, the variable biometric information management server 200 may receive first variable biometric information and second variable biometric information with the information regarding the ID requesting the login command from the mobile terminal 100 (S770), and may compare the first variable biometric information and the second variable biometric information stored therein, and the first variable biometric information and the second variable biometric information received after the login command is requested according to the classification information, and may individually determine equivalence therebetween.

Specifically, the variable biometric information management server 200 may identify the received variable biometric information as first variable biometric information and second variable biometric information according to the classification information, and may compare the first variable biometric information received from the mobile terminal 100 and the stored first variable biometric information, and may determine equivalence therebetween. Likewise, the variable biometric information management server 200 may compare the second variable biometric information received from the mobile terminal 100 and the stored second variable biometric information, and may determine equivalence therebetween (S775).

For example, when average weight data of a user A and weight data of both feet of the user A are collected, the average weight data may be referred to as first variable biometric information, and the weight data of both feet of the user A may be referred to as second variable biometric information. In this case, the variable biometric information management server 200 may determine whether average weight data received from the mobile terminal 100 and stored average weight data are equal to each other, and may determine whether weight data of both feet received from the mobile terminal 100 and stored weight data of both feet are equal to each other. When it is determined that all pieces of variable biometric information are equal to each other (S775-Y), the variable biometric information management server 200 may verify that the login command is valid (S780).

In this case, as pieces of variable biometric information having different information regarding time are complexly compared, pieces of variable biometric information having different classification information may be compared to determine equivalence therebetween, and also, may be compared by diversely setting an average of the first variable biometric information and the second variable biometric information or a complex arithmetic relation between two pieces of variable biometric information.

Specifically, the mobile terminal 100 may calculate an average value or a standard deviation of a real value of the first variable biometric information and a real value of the second variable biometric information, and may match only information regarding a figure or a form of a graph regarding a variation in the average value and the standard deviation of the two pieces of variable biometric information in a specific section, with the information regarding the ID, and may transmit the matched information to the variable biometric information management server 200.

In another example, the variable biometric information management server 200 may calculate a value which is right foot's weight data subtracted from the average weight data, and may compare a subtraction value of variable biometric information received from the mobile terminal 100 and the calculated subtraction value of the variable biometric information, and may determine equivalence therebetween. In this case, the both feet's weight data may be collected by using a biometric information collecting means such as a smart shoe insole.

Accordingly, the security of the authentication procedure can be enhanced by combining different types of variable biometric information, such as user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces, or combining variable biometric information of a plurality of users.

In addition, the security level of the authentication procedure may be selectively determined. Therefore, the security of the authentication procedure can be enhanced by combining different types of variable biometric information or by combining variable biometric information of a plurality of users. In addition, as the security level of the authentication procedure is selectively determined, the authentication procedure can be diversely utilized in an entering authentication to a facility such as an office or school or secure authentication in financial services such as account transfer, payment, etc.

Figure 10:
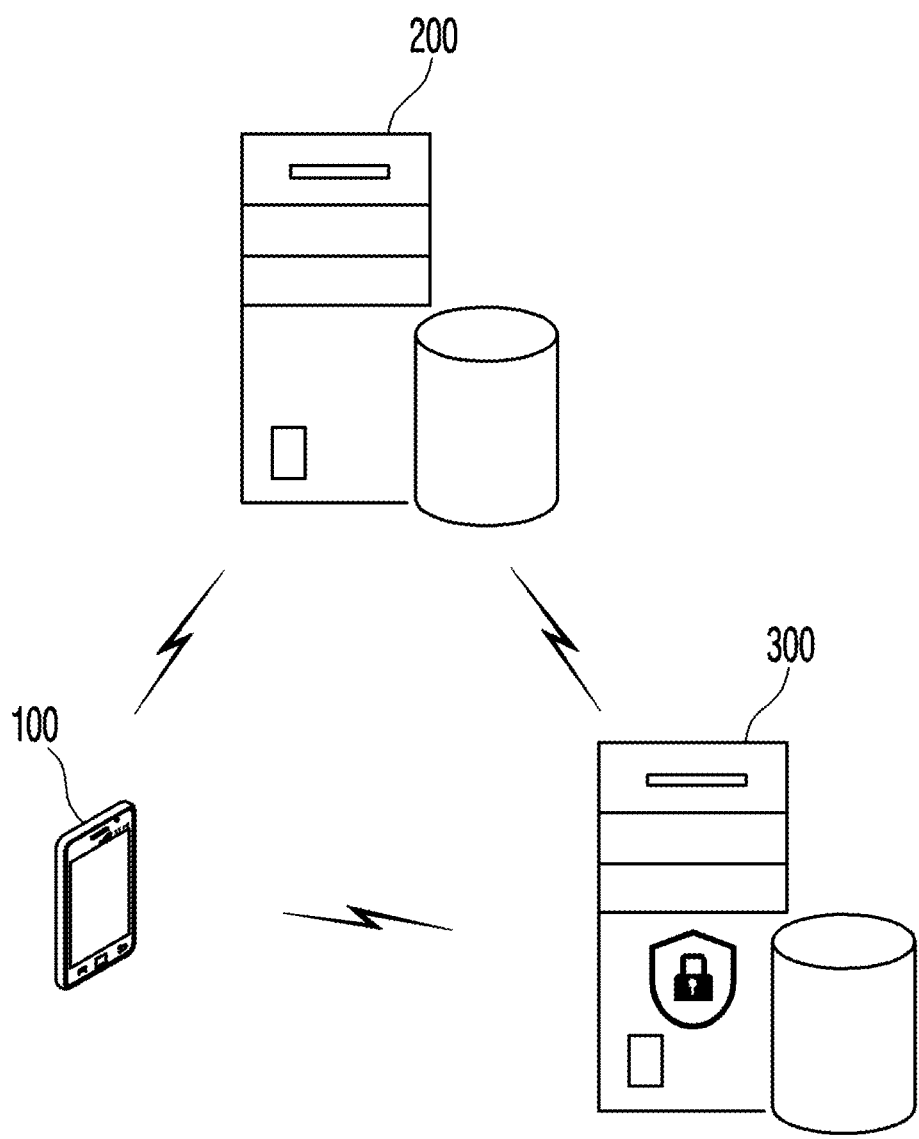
FIG. 10 is a view schematically showing a variable biometric information-based authentication system according to another embodiment of the present disclosure.
Figure 11:
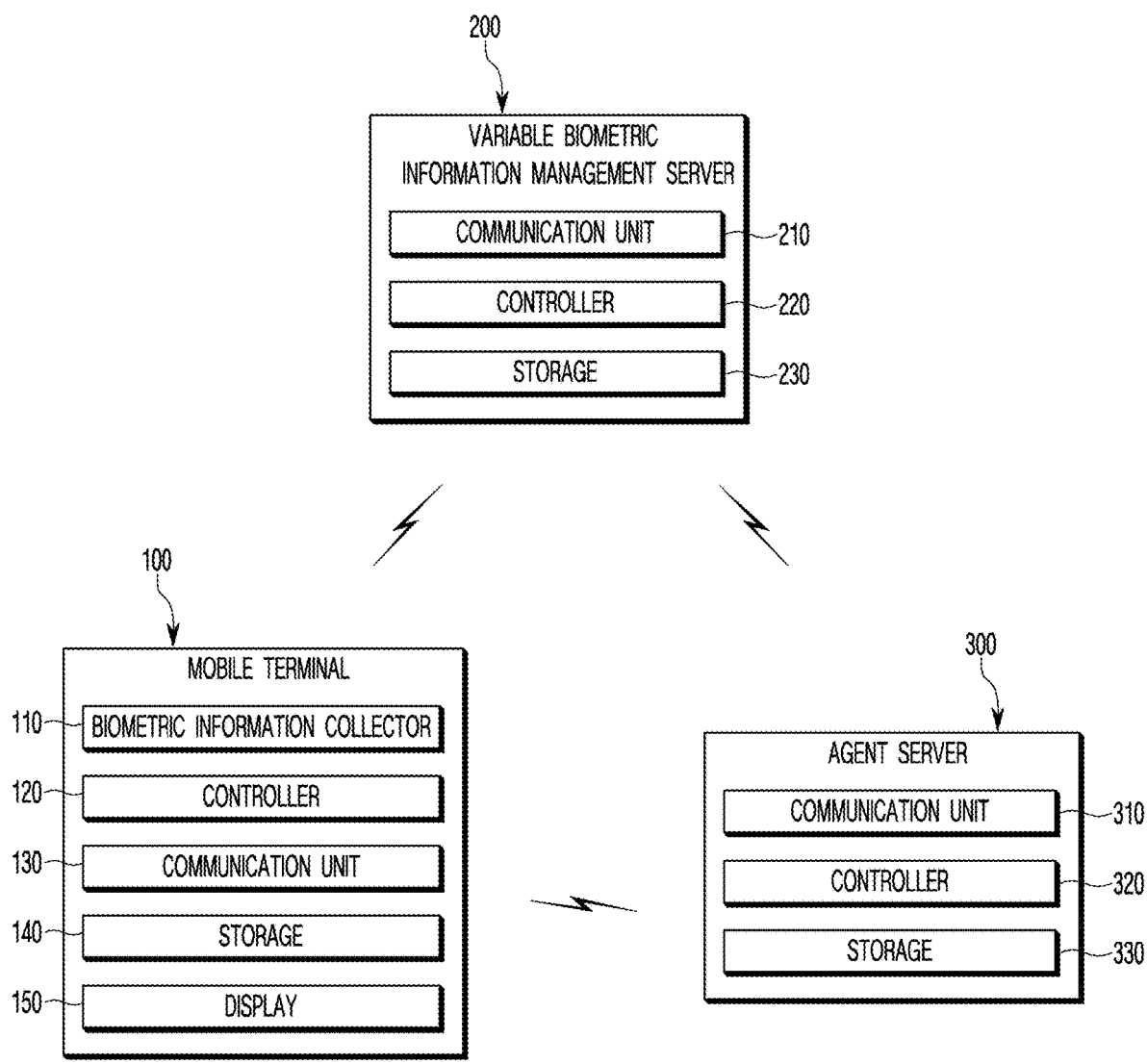
FIG. 11 is a block diagram provided to illustrate a configuration of a variable biometric information-based authentication system according to another embodiment of the present disclosure.

FIG. 10 is a view schematically showing a variable biometric information-based authentication system according to another embodiment of the present disclosure, and FIG. 11 is a block diagram provided to illustrate a configuration of the variable biometric information-based authentication system according to another embodiment of the present disclosure.

Hereinafter, the variable biometric information-based authentication system according to another embodiment will be described, but the difference from the variable biometric information-based system described above with reference to FIGS. 1 to 9 will be highlighted.

Specifically, in the variable biometric information-based authentication system according to another embodiment, the variable biometric information management server 200 may not directly verify validity of a login command regarding a specific ID, and, as shown in FIG. 10, an agent server 300 are additionally configured, in addition to the mobile terminal 100 and the variable biometric information management server 200, and the agent server 300 may verify validity of a login command regarding a specific ID.

That is, the mobile terminal 100 may transmit information regarding an ID and variable biometric information to the variable biometric information management server 200, and may request a login command regarding a specific ID to the agent server 300, and may transmit variable biometric information stored with the information regarding the specific ID used for the requested login command to the agent server 3.

In addition, the variable biometric information management server 200 may receive the information regarding the ID and the variable biometric information and store the same, and may transmit the variable biometric information stored with the information regarding the specific ID used for the login command to the agent server 300 when the agent server 300 verifies validity of the login command regarding the specific ID.

Herein, the mobile terminal 100 may transmit variable biometric information including a real value to the agent server 300 to store the same therein, and, when verification of validity of a login command is requested from a third service server which is separately provided and receives an approval from the user of the mobile terminal, the agent server 300 may not transmit or receive the real value of the variable biometric information to or from the third service server, and may transmit or receive only an arbitrarily calculated data arithmetic value and may verify the validity of the login command.

In this case, the arbitrarily calculated data arithmetic value may include data obtained by separate calculation, and information regarding a figure or a form of a graph indicating a variation in a specific section, and, through this, complexity of the authentication procedure of verifying the validity of a login command may be adjusted and the security level of the authentication procedure may be selectively determined.

For example, when the security level of the authentication procedure for verifying the validity of the login command is a first level, the mobile terminal 100 may transmit variable biometric information including a real value to the variable biometric information management server 200 and the agent server 300, and may request a login command regarding a specific ID to the agent server 300, such that the agent server 300 can compare the variable biometric information including the real values, received from the mobile terminal 100 and the variable biometric information management server 200, and may verify the validity of the requested login command.

In another example, when the security level of the authentication procedure for verifying the validity of the login command is a second level, the mobile terminal 100 may not transmit the real value of the collected variable biometric information to the variable biometric information management server 200, and may transmit only the information regarding a figure or a form of a graph indicating a variation in a specific section along with the information regarding the ID. In this case, the mobile terminal 100 may transmit the real value of the collected variable biometric information to the agent server 300, such that the agent server 300 can extract the information regarding the figure or form of the graph indicating the variation in the specific section by itself. Therefore, when data including the real value of the variable biometric information stored in the mobile terminal 100 is deformed or damaged, a damage resulting therefrom can be minimized or inhibited.

In addition, the agent server 300 stores original data including the real values of the collected variable biometric information as it is, such that the validity of the login command can be verified only with an arithmetic value of data calculated through a predetermined arithmetic procedure according to the security level of the authentication procedure, or the information regarding the figure or the form of the graph indicating the variation in the specific section.

When there is a separate server directly performing a corresponding command or the variable biometric information management server 200 performs the corresponding command, the agent server 300 may transmit information indicating whether the corresponding command is a valid command to the separate server performing the corresponding command or the variable biometric information management server 200, such that the corresponding command is performed.

In addition, when a plurality of agent servers 300 are provided, the respective mobile terminals 100 using different IDs may perform the authentication procedure through the respective agent servers 300.

To achieve this, the agent server 300 may include a communication unit 310, a controller 320, and a storage 330 as shown in FIG. 11.

The communication unit 310 of the agent server may be connected with the mobile terminal 100 and the variable biometric information management server 200 by using a communication network, and may be provided to perform Internet communication.

Specifically, when a login command regarding a specific ID is requested from the mobile terminal 100, the communication unit 310 may receive variable biometric information from the mobile terminal 100 and the variable biometric information management server 200.

The controller 320 of the agent server may control elements of the agent server 300 to perform the overall tasks of the variable biometric information management server 200.

Specifically, when the login command regarding the specific ID is requested from the mobile terminal 100, the controller 320 may control to receive variable biometric information including a real value from the mobile terminal 100 via the communication unit 310, and to store the variable biometric information in the variable biometric information management server 200 along with the information regarding the specific ID. However, the controller 320 may request variable biometric information that does not include a real value and includes only information regarding a figure or a form of a graph indicating a variation in a specific section, and may receive the variable biometric information.

When the variable biometric information is received from the mobile terminal 100 and the variable biometric information management server 200, the controller 320 may extract the information regarding the figure or the form of the graph indicating the variation in the specific section from the variable biometric information received from the mobile terminal 100, and may compare the extracted information regarding the figure or the form of the graph indicating the variation in the specific section, and the variable biometric information received from the variable biometric information management server 200, and may verify validity of the login command regarding the specific ID.

The storage 330 of the agent server may be provided to store programs and data necessary for performing the tasks of the agent server 300.

Through this, in the variable biometric information-based authentication system according to another embodiment, the agent server 300 may selectively determine the security level of the authentication procedure, and may perform the authentication procedure by combining different types of variable biometric information or by combining variable biometric information of a plurality of users more diversely than in the case where the variable biometric information management server 200 performs the authentication procedure, and can enhance the security of the authentication procedure in comparison to the case where the variable biometric information management server 200 performs the authentication procedure.

While embodiments of the present disclosure have been described with reference to the accompanying drawings, specific embodiments for effectively describing the technical idea of the present disclosure are particularly shown and described. Therefore, it will be understood by those of ordinary skill in the art that the present disclosure is not limited to the above-described exemplary embodiments, and various changes in form and details may be made therein without departing from the spirit and scope of the present disclosure as defined by the following claims. In addition, the scope of the present disclosure should be defined not by the embodiments described above but by the appended claims. In addition, the meaning and the scope of the claims and all changes or changed forms derived from equivalents thereto should be interpreted as being included in the scope of the present disclosure.

The invention claimed is:

1. A variable biometric information-based authentication system comprising:
   a mobile terminal configured to generate information regarding an ID that intends to access a facility or information requiring an access authority, and to collect variable biometric information, such that information regarding the 1D and the variable biometric information are stored all together; and
   a variable biometric information management server configured to, when the mobile terminal requests a login command regarding the ID, verify validity of the login command regarding the ID based on the variable biometric information,
   wherein the variable biometric information management server is configured to determine whether a specific ID is an ID of a first security level or an ID of a second security level based on the information regarding the ID, the ID of the first security level allowing the validity of the login command regarding the ID to be verified based on one type of variable biometric information, the ID of the second security level allowing the validity of the login command regarding the ID to be verified based on a combination of two or more types of variable biometric information or a complex arithmetic relation, and
   wherein, when the specific ID is the ID of the first security level, the mobile terminal is configured to collect the variable biometric information, and to transmit only information regarding a figure or a form of a graph indicating a variation in a specific section, without transmitting a real value of the collected variable biometric information to the variable biometric information management server.

2. The variable biometric information-based authentication system of claim 1, wherein the variable biometric information management server is configured to:
   when the information regarding the ID matched with the variable biometric information and stored, and the variable biometric information including only the information regarding the figure or the form of the graph are received, store the received information regarding the ID and the variable biometric information;
   when a login command regarding the specific ID is requested, receive variable biometric information for verifying validity of the login command from the mobile terminal;
   compare the received variable biometric information and the figure or the form of the graph included in the stored variable biometric information including only the information regarding the figure or the form of the graph on a real time basis, and to verify the validity of the login command.

3. The variable biometric information-based authentication system of claim 2, wherein the variable biometric information management server is configured to accumulate and store the variable biometric information including only the figure or the form of the graph according to the information regarding the ID, and, when the mobile terminal requests the variable biometric information stored for the specific ID to be discarded, the variable biometric information management server is configured to discard the variable biometric information stored for the specific ID, and to accumulate and store the variable biometric information transmitted with the information regarding the specific ID after the stored variable biometric information is discarded, according to the information regarding the ID.

4. The variable biometric information-based authentication system of claim 1, wherein, when the specific ID is the ID of the first security level, the mobile terminal is configured to collect and store the variable biometric information in the unit of a predetermined time, and to add information regarding time to the variable biometric information and to store the information, and
   wherein the mobile terminal is configured to transmit the information regarding the time and the information regarding the figure or the form of the graph indicating the variation in the specific section, without transmitting the real value of the collected variable biometric information to the variable biometric information management server.

5. The variable biometric information-based authentication system of claim 4, wherein, when the login command regarding the ID is requested, the variable biometric information management server is configured to compare information regarding time, added to variable biometric information received from the mobile terminal, and the information regarding the time, added to the variable biometric information received from the variable biometric information management server, and to determine equivalence therebetween, and, when it is determined the respective pieces of information regarding the times are equal to each other, the variable biometric information management server is configured to determine equivalence between the respective pieces of variable biometric information, and to verify the validity of the login command regarding the ID.

6. The variable biometric information-based authentication system of claim 1, wherein, when the specific ID is the ID of the second security level, the mobile terminal is configured to collect the two or more types of variable biometric information, and to match respective pieces of classification information with the information regarding the ID, such that the respective types of variable biometric information are identified.

7. The variable biometric information-based authentication system of claim 6, wherein, when the specific ID is the ID of the second security level, the variable biometric information management server is configured to receive, from the mobile terminal, first variable biometric information and second variable biometric information in which different types of classification information are matched with the information regarding the ID, and to store the first and second variable biometric information, and
   wherein, when the login command regarding the ID is requested, the variable biometric information management server is configured to receive first variable biometric information and second variable biometric information matched with information regarding the ID requesting the login command from the mobile terminal, and to individually determine whether the stored first variable biometric information and second variable biometric information are equal to the received first variable biometric information and second variable biometric information, and to verify the validity of the login command regarding the ID.

8. The variable biometric information-based authentication system of claim 1, wherein, when the mobile terminal is connected to a short range communication network, the mobile terminal is configured to transmit the stored variable biometric information to the variable biometric information management server at predetermined time intervals.

9. The variable biometric information-based authentication system of claim 1, wherein the variable biometric information comprises one or more pieces of information from among user's weight, body fat percentage, blood pressure, temperature, breathing rate, heart rate, blood glucose, muscle mass, total body water, protein, abdominal visceral fat, skeletal muscle mass, basal metabolic rate, exercise, number of steps, sleeping pattern, weight load pattern of both feet, and paces.

* * * * *